United States Patent
Majeed et al.

(10) Patent No.: US 10,407,401 B1
(45) Date of Patent: Sep. 10, 2019

(54) PROCESS FOR SYNTHESIS OF OROXYLIN A

(71) Applicants: Muhammed Majeed, Edison, NJ (US); Kalyanam Nagabhushanam, East Windsor, NJ (US); Rajendran Ramanujam, Bangalore (IN); Hosahalli Prabhakara Hemantha, Bangalore (IN)

(72) Inventors: Muhammed Majeed, Edison, NJ (US); Kalyanam Nagabhushanam, East Windsor, NJ (US); Rajendran Ramanujam, Bangalore (IN); Hosahalli Prabhakara Hemantha, Bangalore (IN)

(73) Assignee: SAMI LABS LIMITED, Bangalore (IN)

(*) Notice: Subject to any disclaimer, the term of this patent is extended or adjusted under 35 U.S.C. 154(b) by 0 days.

(21) Appl. No.: 16/055,054

(22) Filed: Aug. 4, 2018

(51) Int. Cl.
*C07D 311/30* (2006.01)

(52) U.S. Cl.
CPC .................. *C07D 311/30* (2013.01)

(58) Field of Classification Search
CPC ..................................... C07D 311/20
See application file for complete search history.

(56) References Cited

PUBLICATIONS

Dong, Chem Biol Drug Des, 2016, vol. 87, 946-857. (Year: 2016).*

* cited by examiner

*Primary Examiner* — D Margaret M Seaman

(57) ABSTRACT

Disclosed is a novel, simple, scalable and environment friendly process for the synthesis of Oroxylin A from Baicalin. Baicalin is esterified to obtain a methyl ester which is further selectively methylated to provide Oroxylin A glucuronide methyl ester which on de-glycosylation results in the formation of Oroxylin A.

5 Claims, No Drawings

PROCESS FOR SYNTHESIS OF OROXYLIN A

BACKGROUND OF THE INVENTION

Field of the invention

The invention in general relates to a novel process for the synthesis of Oroxylin A. More specifically, the present invention relates to novel process for the synthesis Oroxylin A from Baicalin.

Description of Prior Art

*Oroxylum indicum*, is a traditional herb, well known in ancient ayurvedic literature. It exhibits a wide range of therapeutic functions viz. antimicrobial, antidiabetic, hepato-protective, anti-inflammatory, anti-carcinogenic, immunomodulatory, nephro-protective, cardio-protective, etc. (Ahad, A. Ganai, A. A.; Sareer, O.; Najim, M. Z., Kauzar, M. A.; Mohd, M.; Siddiqui, W. A. *Journal of pharrnaceutical research and opinion*, 2012, 2(10), 163-172). It is reported to contain a variety of secondary metabolites namely, flavonoids, iso-flavonoids, glycosides, tannins, terpenoids, stilbenes and more. Among about 50 flavonoids isolated from its extracts so far, Baicalein, Chrysin and Oroxylin A are the major ones to go with minor flavonoids such as Biochanin A, 8,8'-bis-Baicalein, 6-hydroxy Luteolin, Oroxoloside methyl ester, Baicalein-7-O-glucoside etc. Ellagic acid, Ursolic acid, β-Sitosterol and Aloe-Emodin are some of the other useful phytochemicals present in the extracts of *Oroxylum indicum* (Deka, D. C.; Kumar, V.; Prasad, C.; Kumar, K.; Gogoi, B. J.; Singh, L.; Srivastava, R. B. *J. Appl. Pharm. Sci.*, 2013, 3, S104-S112).

Among different flavonoids belonging to the *Oroxylum indicum* family, a mono-O-methylated flavone, Oroxylin A (5,7-dihydroxy, 6-methoxy flavone) has been the subject of several biophysical research owing to its immense medicinal values. Apart from *Oraryhun indicum* as mentioned before, *Scutellaria baicalensis* is another natural source of Oroxylin A.

Oroxylin A shows wide range of therapeutic applications ranging from anticancer, anti-obesity, antioxidant, anti-inflammatory, to cardio protective and neuroprotective roles. The biological, effects of Oroxylin A are well documented in the following prior arts:
1. Chen, Y-C.; Yang, L-L.; Lee, T. J-F. *Biochem, Pharm.* 2000, 59. 1445-1457;
2. Liu, P.-W.; Chen, M-F.; Tsai, A. P-Y.; Lee, T. J. F. PLoS ONE, 2012, 7, 1-8 (doi:10.1371/journal-.pone.0050363).
3. Song, X.; Chen, Y.; Sun, Y.; Lin, B.; Qin, Y.; Hui, H.; Li, Z.; You, Q.; Lu, N.; Guo, Q. *Pharmacol. Rep.* 2012, 64, 1189-11993.
4. Sun, Y.; Lu, N.; Ling, Y.; Gao, Y.; Chen, Y.; Wang, L.; Hu, R.; Qi, Q.; Liu, W.; Yang, Y.; You, Q.; Guo, Q. *Eur. J. Pharm.* 2009, 603, 22-28
5. Liu, C-H.; Chen, M-F.; Tseng, T-L.; Chen, L-G.; Kuo, J-S.; Lee, T. J-F. *Evid. Based Complement. Alternat. Med.* Volume 2012, doi:10.1155/2012/408187).
6. Yoon, S. Y.; Chun, M. S.; Lee, Y. S.; Park, H. I., Shin, C. Y.; Ryu, J. H.; Cheong, J. H. *Biomol. Ther.* 2008, 16, 343-350.

Another micro-component of *Oroxylum indicum*, Oroxyloside methyl ester or Oroxylin A glucuronide methyl ester (OAGME), is also reported to exhibit a-giycosidase inhibitory activity (EP1986670 B1) and anti-ulcer properties (US 7855200; US2007/0213281 A1).

About half of the best selling pharmaceuticals and drugs are either natural or closely related to natural products or compositions thereof. Interestingly, plant derived metabolites have been the foundation for several of the modern drug discovery programs (Deka, D. C.; Kumar, V.; Prasad, C.; Kumar, K.; Gogoi, B. J.; Singh, L.; Srivastava, R. B. J. Appl. Pharm. Sci., 2013, 3, S104-S112). This shows the global inclination towards natural ingredients in drugs and this tendency is also appearing in cosmetic and nutraceuticals fields. Development of a novel chemistry is essential to segregate complex bio-based feedstock and convert them into desired chemical components for use in pharma and other fields. Oroxylin A is traditionally isolated from *Oroxylum indicum* with a yield of only 0.7% (U.S. Pat. No. 7,855,200). Hence, a facile process where it may be produced in good quantity so as to carryout thorough biological screening is warranted. Development of such a method would be crucial if these flavones are to be used in nutraceuticals and pharmaceutical formulations.

There are only a few schemes available in the literature on the preparation of Oroxylin A. The following prior art documents disclose the synthesis of Oroxylin A and related analogs
1. Huang, W-S.; Chien, P-Y.; Yang, C-H.; Lee, A-R. *Chem. Pharm. Bull.*, 2003, 51, 339-340
2. Shaw, J.; Lee, A-R.; Huang, W-H. 2004, US 2004/0242907 A1
3. Pham, T-A. N.; Che, H.; Phan, P-T. T.; Le, J-W.; Kim, S-S.; Park, H. *Bioorg. Med. Chem. Lett.* 2012, 22, 2534-2535.
4. Gao, H.; Nishioka, T.; Kawabata, J.; Kasai, T. *Biosci. Biotechnol. Biochem.*, 2004, 68, 369-375.
5. Varady, J. *Tett. Lett.*, 1965, 6, 4281-4282.
6. Qidong, Y.; Zhiyu, L.; Yang, B.; Fu, W.; Qinglong, G. CN101508689A.
7. Fujita, R.; Hanaya, K.; Higashibayashi, S.; Sugai, T. *Heterocycles*, 2018, in press DOI: 10.3987/COM-18-S(T)59.

However, they suffer drawbacks such as lengthy reaction sequences, column purification of intermediates, harsh conditions, low yields, expensive starting materials and importantly, in some cases, ambiguity of the product itself.

Green chemistry principles promote reduction of toxic waste, utilization of renewable resources, reduction of pollution, recover, reuse and recycle of reagents, atom economy and use of biodegradable reagents. Thus, this invention discloses a novel, easy and environmental friendly process for the synthesis of Oroxylin A Baicalin which strives on the use of renewable natural feed stock, produce non-hazardous byproducts and development of atom economical process to achieve the target molecule so as to abide with the green chemistry principle to the possible extent.

It is a principle objective of the invention to disclose a novel process for the synthesis of Oroxylin A from Baicalin.

The invention fulfils the above mentioned objective and provides further related advantages.

SUMMARY OF THE INVENTION

The present invention discloses a novel process for the synthesis of Oroxylin A. More specifically, the invention discloses a simple, scalable, environment friendly process for the synthesis of Oroxylin A from Baicalin. Baicalin is esterified to obtain a methyl ester which is further methylated to provide Oroxylin A glucuronide methyl ester which on de-glycosylation results in the formation of Oroxylin A.

Other features and advantages of the present invention will become apparent from the following more detailed description, taken in conjunction with the accompanying images, which illustrate, by way of example, the principle of the invention.

DESCRIPTION OF THE MOST PREFERRED EMBODIMENTS

In the most preferred, embodiment the invention discloses a novel process for the synthesis of Oroxylin A as represented by STR#1, comprising steps of:

a) esterifying Baicalin, as represented by STR#2 using acid-alcohol mixture to obtain a compound as represented by STR#3,

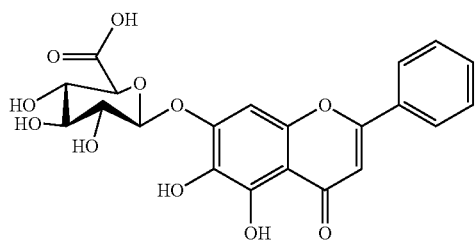

STR#2

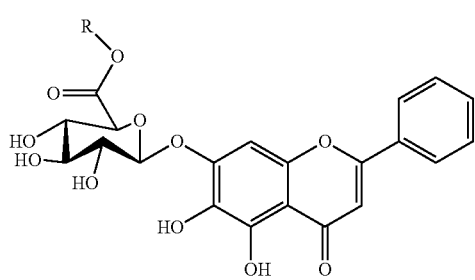

STR#3 wherein 'R' is selected from methyl, ethyl, n-propyl or isopropyl;

b) methylating the compound of step a) represented by STR#3 using a methylating agent in the presence of a base to obtain a compound as represented by STR#4,

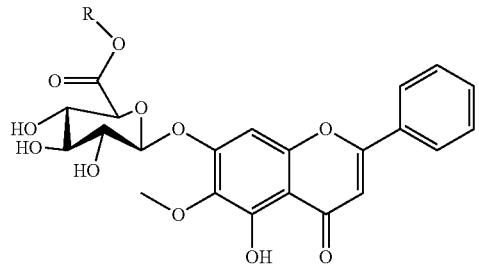

STR#4 wherein 'R' is selected from methyl, ethyl, n-propyl of isopropyl;

c. subjecting the compound of step b, represented by STR#4 to acid hydrolysis to obtain the product Oroxylin A as represented by STR#1

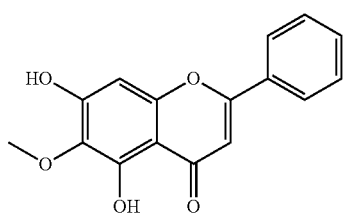

STR#1

In a related embodiment the acid is selected from the group consisting of, but not limited to, sulphuric acid, p-toluene sulfonic acid, hydrochloric acid, methanesulfonic acid, and trifluroacetic acid. In another related embodiment alcohol is selected from the group consisting of, but not limited to methanol, ethanol, n-propanol and isopropanol. In yet another related embodiment the methylating agents are selected from the group consisting of, but not limited to, dimethyl sulphate, methyl iodide, dimethyl carbonate, diazomethane and trimethylsilyldiazomethane. In another preferred embodiment the base is selected from the group consisting of, but not limited to potassium carbonate, sodium carbonate, cesium carbonate, triethyl amine and diisopropyl amine.

The specific examples included herein below illustrate the aforesaid most preferred embodiments of the present invention.

Example 1 Synthesis of Oroxylin A

Rationale

There are two distinct synthetic schemes reported on the preparation of Oroxylin A available in the literature. Huang and co-corkers reported flavones' synthesis via the established chalcone route (Scheme 1) (Huang, W-S.; Chien, P-Y.; Yang, C-H.; Lee, A-R. Chem. Pharm. Bull., 2003, 51, 339-340; Shaw, J.; Lee, A-R.; Huang, W-H. 2004, US 2004/0242907 A1). Starting from commercially available 3,4,5-trimethoxyphenol, the authors arrived at 3,4,5-trimethylbaicalein through a multistep synthesis. The final step to obtain Oroxylin A from here would be a selective bis-demethylation (at 5- and 7-positions) which the authors have reported to have obtained in 88% yield using 47% HBr under reflux. Using this procedure, Pham and co-workers prepared Oroxylin A and its analogs far a study on their inhibitory activity on iNOS mediated nitric oxide production (Pham, T-A. N.; Che, H.; Phan, P-T. T.; Le, J-W.; Kim, S-S.; Park, H. Bioorg. Med. Chem. Lett. 2012, 22, 2534-2535).

Scheme 1: Reported routes for the synthesis of Oroxylin A
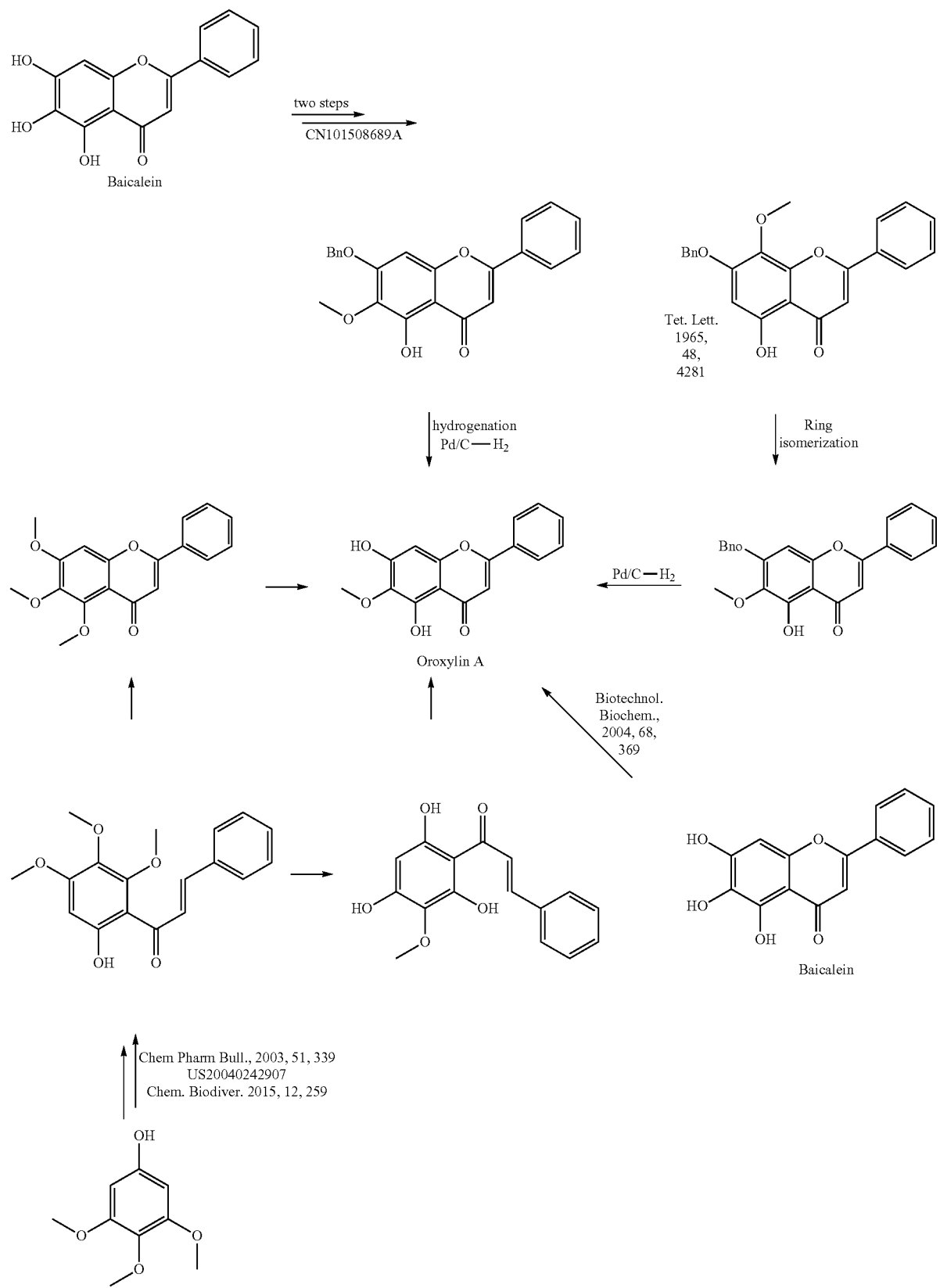

The main requirement in the above process is the selectivity in ether cleavage. Although the above authors claim to have obtained Oroxylin A, a comparison of the $^1$H NMR data furnished in those papers with the $^1$H NMR data of natural Oroxylin A published (Kim, D. H.; Jeon, S. J.; Son, K. H.; Jung, J. W.; Lee, S.; Yoon, B. H.; Lee, J-J.; Cho, Y-K.; Cheong, J. H.; Ko, K. H.; Ryu, J. H. Neurobiol. Learn. Mem. 2007, 87, 536-546) do not match. Since there are three methoxy groups at $5^{th}$, $6^{th}$ and $7^{th}$ positions of the trimethylbaicalein, the authors claim that deprotection under HBr/AcOH/reflux condition cleaves the ether groups exclusively at $5^{th}$ and $7^{th}$ positions, retaining the methoxy group at $6^{th}$ position intact, thereby yielding Oroxylin A (STR#1). The rationale behind this prediction is not understood. Because, there is another possible isomer-5,6-dihydroxy,7-methoxyflavone also known as Negletein (STR#5) which differs from Oroxylin A only in the position of the methoxy group (at C-7 instead of C-6).

Careful $^1$H NMR interpretation is necessary to distinguish Negletein (STR#5) and Oroxylin A (STR#1). Specifically, H3 and H8 protons appear at 6.63 and 6.97 ppm respectively for Oroxylin A (Kim, D. H.; Jeon, S. J.; Son, K. H.; Jung, J. W.; Lee, S.; Yoon, B. H.; Lee, J-J.; Cho, Y-K.; Cheong, J. H.; Ko, K. H.; Ryu, J. H. Neurobiol. Learn. Mem. 2007, 87, 536-546 Fuentes, R. G.; Arai, M. A.; Sadhu, S. K.; Ahmed, F.; Ishibashi, M. J. Nat. Med., 2015, 69, 589-594; Joshi, B. S.; Gawad, D. H. Proc. Ind. Acd. Sci., 1977, 86, 41-44), whereas for Negletein, H3 and H8 NMR signals are very close and appear at 6.92 and 6.96 ppm (He, G.; Gao, Y.; Li, C.; Wu, G.; Li, Y.; Dong, L. Huang, C.; Chen, H. Tet. Lett. 2016, 57, 2001-2005). Similar chemistry was adopted by Tan and Co-workers (Tan, Schrader, K. K.; Khan, I. A.; Rimando, A. M. Chem. Biodiver., 2015, 12, 259-272.) and interestingly, in the NMR data they have reported, a clear difference of 0.3 ppm between H-3 and H-8 signals can be seen although the peak positions are different (6.70 and 6.41 ppm). This dissimilarity in the NMR data of the outcome of exactly the same reaction, but by different research groups prompted us to investigate the feasibility of the process in our hands.

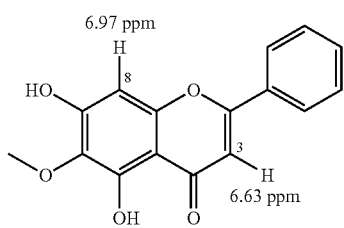

STR#1

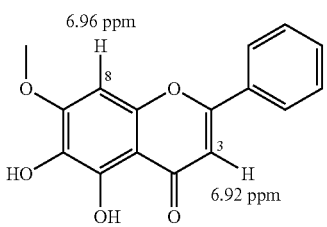

STR#5

Thus, we prepared 5,6,7-trimethylbaicalein in a similar way and tried demethylation under 47% HBr/AcOH conditions. However, our best efforts turned futile to obtain the right compound as we always ended up getting Negletein instead of intended Oroxylin A. In a control experiment, when a reaction of 5,6,7-trimethylbaicalein in 47% HBr/Acetic acid was carried out at 80° C. for 3 h, we could see only a mono-demethylation at $5^{th}$ position yielding 6,7-dimethylbaicalein as a predominant product (Scheme 2). This was isolated and characterized by $^1$H NMR where a singlet at 12.76 ppm was seen which is a characteristic of 5-OH proton [$^1$H NMR (300 MHz, DMSO-d$_6$) δ ppm: 12.76 (s, 1H, 5-OH), 8.08-8.11 (m, 2H, Ar), 7.57-7.59 (m, 3H, Ar), 7.04 (s, 1H), 6.98 (s, 1H), 3.92 (s, 3H, OMe), 3.72 (s, 3H, OMe)]. When the reaction was run at 110° C. for 3 h, we could see formation of a polar spot in TLC (CHCl$_3$:MeOH-9:1) via bis-demethylation giving rise to Negletein [$^1$H NMR (300 MHz, DMSO-d$_6$) δ ppm: 12.48 (s, 1H, 5-OH), 8.76 (s, 1H, 6-OH), 8.05-8.08 (m, 2H, Ar), 7.55-7.57 (m, 3H, Ar), 6.97 (s, 1H), 6.93 (s, 1H), 3.90 (s, 3H, OMe)]. This is in close agreement with the NMR data of Negletein published by He and co-workers (He, G.; Gao, Y.; Li, C.; Wu, G.; Li, Y.; Dong, L.; Huang, C.; Chen, H. Tett. Lett. 2016, 57, 2001-2005). Exactly similar mode of such step wise demethylation has also been reported by Righi et al., further strengthening our observation (Righi, G.; Antonioletti, R.; Silvestri, I. P.; D'Antona, N.; Lambusta. D.; Bovicelli, P. Tetrahedron, 2010, 66, 1294-1298).

Scheme 2 - Demethylation of 5,6,7-trimethylbaicalein under different conditions

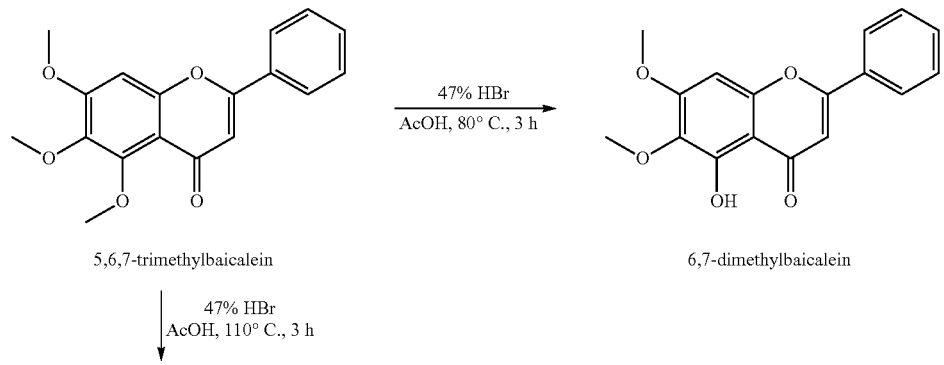

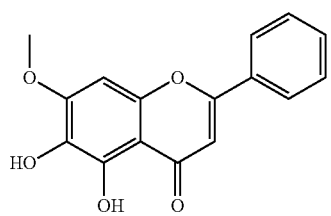

Negletein
100% conversion,
80% isolated yield

+

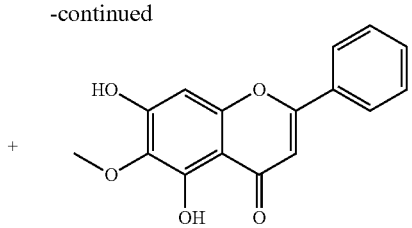

Oroxylin A
0%

This ambiguity was thoroughly studied by Panhekar et al., who showed that the outcome of HBr mediated deprotection of 5,6,7-trimethylbaicalein is not Oroxylin A as reported in the papers mentioned above, but Negletein only (Panhekar, D.; Mahale, G. D.; Renalson, K. S. Satpute, S. J. Chem. Pharm. Res., 2015. 7, 174-180). They have substantiated this observation through mass spectrometry, $^1$H, $^{13}$C and NOESY NMR analyses. This mode of deprotection of 5,6,7-trimethylbaicalein yielding Negletein was also observed by Waghmode and co-workers (Waghmode, S. B.; Mahale, G.; Patil, V. P.; Renalson, K.; Singh, D. Synth. Commun., 2013, 43, 3272-3280). Such ambiguity in chemistry deters one to choose this process to synthesize Oroxylin A.

Panhekar et al., while solving the uncertainty in the above process, validated another protocol reported in CN101508689A starting from Baicalein. This involves selective benzylation of the hydroxy group at 7$^{th}$ position followed by methylation of 6-OH and finally debenzylation to afford exclusively Oroxylin A in a moderate yield (Scheme 1).

Methylation of Baicalein using excess MeI/K$_2$CO$_3$ in acetone under reflux (Scheme 1) affords Oroxylin A albeit as a minor product (15% yield) along with the major one-5-hydroxy,6,7-dimethoxy-flavone (60% yield) (Gao, H.; Nishioka, T. Kawabata, J.; Kasai, T. Biosci. Biotechnol. Biochem., 2004, 68, 369-375). However, this non-exclusive method is not an efficient process to synthesize Oroxylin A.

Varady demonstrated the concept of ring isomerization of flavones under alkaline medium and put to use for the preparation of Oroxylin A from suitably substituted Wogonin (Scheme 1). Briefly, 7-OH of Wogonin was benzylated, 8-OH was methylated selectively and then the resulting 7-benzyl, 8-methyl-wogonin was subjected to ring isomerisation under basic and anhydrous condition to afford 7-benzyl-Oroxylin A which upon catalytic hydrogenation, afforded Oroxylin A (Varady, Tett. Lett., 1965, 6, 4281-4282).

As detailed above, there are only a countable number of methods directed towards Oroxylin A synthesis. However, they suffer drawbacks such as lengthy reaction sequences, column purification of intermediates, harsh conditions, low yields, expensive starting materials and importantly, in some cases, ambiguity of the product itself. Further, they do not comply with our motivation of developing a green process and thus we had to choose an alternate starting material and develop a new chemistry.

Synthesis of Oroxylin A from Baicalin

With the above background, we came across a glycoflavonoid-Baicalin or Baicalein-7-O-glucuronide (STR#2) which exists in the bark extracts of *Oroxylum indicum*. Similar to other flavones of this family, Baicalin also possesses several pharmacological advantages such as anxiolytic like effect and anti-cancer properties. Besides its medicinal values, it is commercially cheap (USD 80 per KG) and is an excellent starting material for the preparation of several other flavonoids. Microbial transformation of Baicalin and Baicalein to other flavones including Oroxylin A has been reported by Kostrzewa-Suslow et.al. The reaction is very slow (6 days) with only a moderate yield (Kostrzewa-Suslow, E.; Dmochowska-Gladysz, J.; Oszmianski, J. J. Mol. Cat. B: Enzym., 2007, 49, 113-117). Again, the $^1$H NMR data furnished here for Oroxylin A is inconsistent with reported data for Oroxylin A.

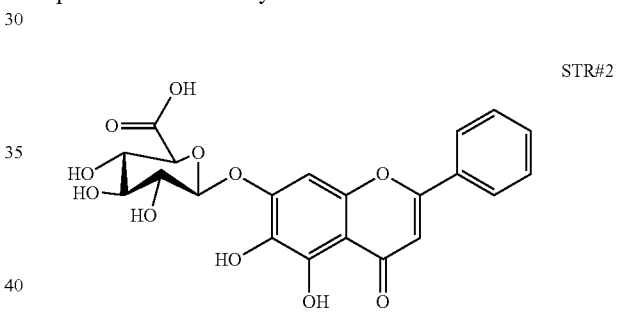

STR#2

We hypothesized that Baicalin can be an excellent starting material for Oroxylin A as well as Oroxyloside methyl ester or Oroxylin A glucuronide methyl ester (OAGME). As described above, we were motivated to develop a semi synthetic green chemistry for the preparation of these pharmacologically useful flavones starting from a natural feed stock to which Baicalin seemed to fit perfectly. Advantage of using Baicalin as a precursor to our targets is that the starting material contains a natural protection for 7-OH in the form of glucuronide, leaving 5-and 6-OH groups free. Gratifyingly, the 6-OH group possesses a superior nucleophilicity over 5-OH group which enables selective alkylation at 6-OH, for example methylation in the case of Oroxylin A. This may also be due to the fact that 5-OH is intramolecularly hydrogen bonded to the C-4 carbonyl group which hinders its nucleophilicity unless subjected to forcible alkylation conditions such as strong bases, excess alkylating reagents and higher reaction temperatures. The final step would be cleavage of the glucuronide group which can be operated using a mineral acid which is acceptable by the green chemistry principles.

In the first step of the present work, commercially available Baicalin (STR#2) was esterified in refluxing methanol/THF mixture containing a catalytic amount of conc. H$_2$SO$_4$or hydrochloric acid or trifluroacetic acid. In a similar way, methanol can be replaced with other alcohols such as ethanol and isopropyl alcohol to obtain the respective esters. After bringing the reaction mixture to room temperature, the precipitated Baicalin methyl ester (STR#3) was isolated by filtration and the material was pure enough to take for next step as such.

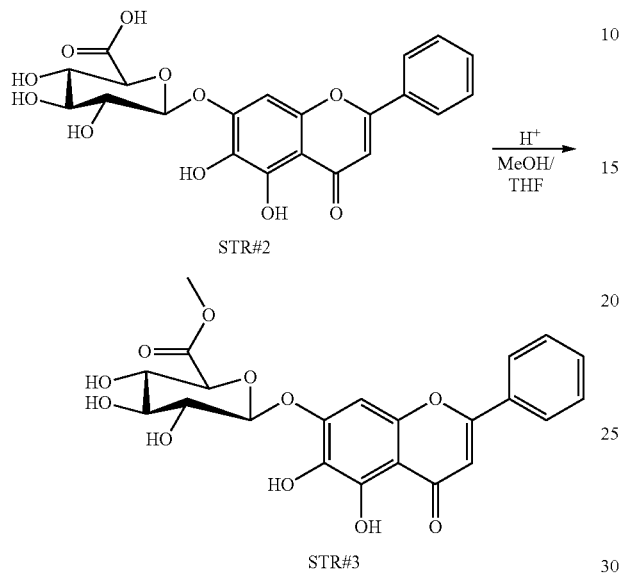

The NMR data of Baicalin methyl ester is given below:

NMR: $^1$H NMR (300 MHz, DMSO-$d_6$) δ ppm: 8.11 (m, 2H, Ar), 7.5 (m, 3H, Ar), 7.0 (s, 1H, H-8), 6.9 (s, 1H, H-3), 5.25 (d, 1H, sugar H-1), 4.25 (d, 1H, sugar H-5), 3.28-3.50 (m, 3H, sugar H-2, H-3, H-4); $^{13}$C NMR (75 MHz, DMSO-$d_6$) δ ppm: 182.97, 169.65, 163.96, 151.66, 149.63, 147.24, 132.48, 131.25, 131.01, 129.59, 126.81, 106.57, 105.20, 100.20, 94.07, 75.70, 75.47, 73.18, 71.84, 52.47. Mass: Expected: 460.38 Da; Observed: 461.10 (M+H)$^+$.

In the second stage, 6-OH was methylated using dimethyl sulphate or methyl iodide in the presence of a base. Under the conditions optimized, alkylation was achieved selectively at 6-OH and a simple work-up afforded OAGME (STR#4) in almost quantitative yield. This crude was triturated in suitable solvent and filtered to obtain analytically pure sample. The process can be easily scaled up and the pure product can be obtained after a simple work-up and trituration with suitable solvents.

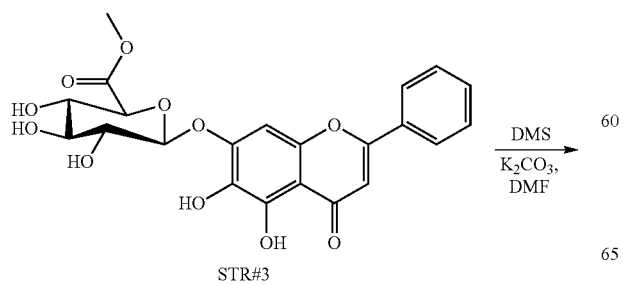

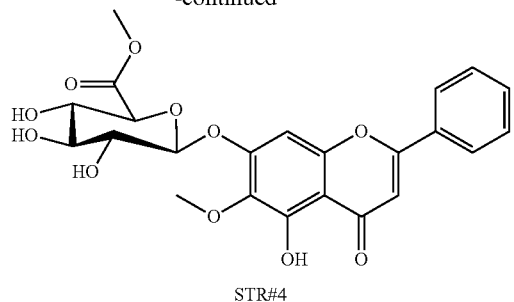

The NMR of OAGME is provided below:

NMR: $^1$H NMR (300 MHz, DMSO-$d_6$) δ ppm: 12.95 (1H, s, 5-OH), 8.19 (m, 2H, Ar), 7.73 (m, 3H, Ar), 7.15 (s, 1H, H-8), 7.07 (s, 1H, H-3), 5.25 (d, 1H, sugar H-1), 5.30-5.67 (m, 3H, Sugar-OH protons), 4.27 (d, 1H, sugar H-5), 3.80 (s, 3H, Ar-OMe), 3.70 (s, 3H, Ar-OMe), 3.34-3.48 (m, 3H, sugar H-2, H-3, H-4); $^{13}$C NMR (75 MHz, DMSO-$d_6$) δ ppm: 182.96, 169.63, 164.19, 156.62, 153.03, 152.74, 133.02, 132.65, 131.08, 129.62, 126.89, 106.60, 105.47, 99.74, 94.45, 76.09, 75.70, 73.21, 71.75 60.77, 52.45. Mass: Expected: 474.41 Da; Observed: 475.12 (M+H)$^+$.

Finally, glucuronide part was cleaved out from the aglycone using an acid mediated hydrolysis and the resulting Oroxylin A (STR#1) was isolated by a flash chromatography. The by-product of this step is methyl glucuronate (STR#6) which is a biodegradable material and can also be a useful synthetic intermediate. Thus, the process described here abides several of the green chemistry criteria such as high yielding individual steps, natural raw materials, safe reaction conditions, non-toxic byproducts among others.

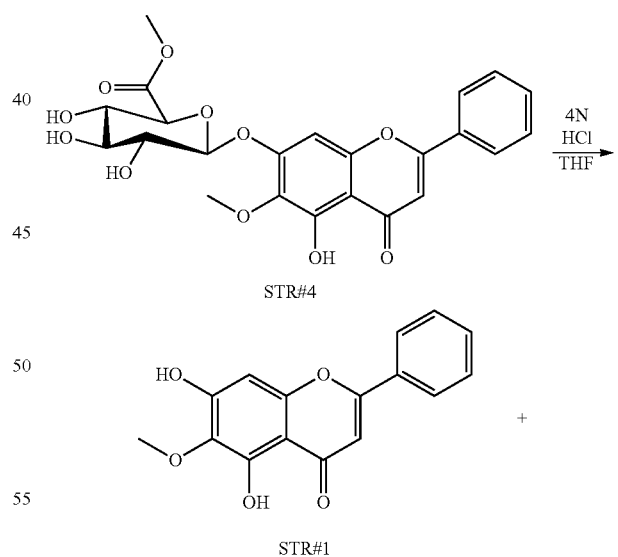

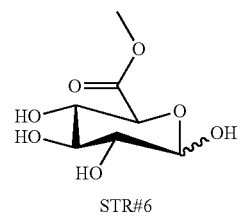

The molecular integrity of the synthetic Oroxylin A prepared by the present method was confirmed by NMR analyses. NMR data of the Oroxylin A made by the present method was in agreement with the reported data on Oroxylin A isolated from a natural source (Kim, D. H.; Jeon, S. J.; Son, K. H.; Jung, J. W.; Lee, S.; Yoon, B. H.; Lee. J-J.; Cho, Y-K.; Cheong, J. H.; Ko, K. H.; Ryu, J. H. Neurobiol. Learn. Mem. 2007, 87, 536-546).

NMR: $^1$H NMR (300 MHz, DMSO-$d_6$) δ ppm: 12.91 (s, 1H, 5-OH), 10.79 (s, 1H, 7-OH), 8.05 (m, 2H, Ar), 7.58 (m, 3H, Ar), 6.96 (s, 1H, H-8), 6.62 (s, 1H, H-3), 3.74 (s, 3H, OMe); $^{13}$C NMR (75 MHz, DMSO-$d_6$) δ ppm: 182.71, 163.64, 158.02, 153.19, 152.99, 132.45, 131.89, 131.16, 129.57, 126.84, 105.11, 94.85, 60.41. Mass: Expected: 284.26 Da; Observed: 285.07 (M+H)$^+$.

Procedures

Step 1: Baicalin to Baicalin Methyl Ester

5 G of Baicalin was suspended in MeOH:THF (150 mL, 2:1 ratio) to which 2-3 drops of conc. $H_2SO_4$ was added and the reaction was stirred at 80° C. for 6 h. Progress of the reaction was followed by TLC. Upon completion of the reaction, solvent was evaporated and the residue was triturated in hexane, filtered and suck dried (4.9 Grams; 95%).

Step 2: Baicalin Methyl Ester to OAGME by Methylation 4.9 Grams of Baicalin methyl ester was dissolved in 35 mL of DMF to which $K_2CO_3$ (2.0 eq) was added. It was cooled and 1.5 eq. of dimethyl sulphate was added and the reaction was allowed to stir over night at room temperature. After the completion of reaction (TLC), the mixture was poured with stirring into cold water containing, dilute HCl and the precipitate was filtered, suck dried to get OAGME (4.6 Grams; 91%). The material can be purified by trituration with Ethanol.

Step 3: OAGME to Oroxylin A by Deglycosylation 2.0 grams of OAGME was suspended in 20 mL water to which 2 mL conc. $H_2SO_4$ was added drop-wise. The resulting exothermic reaction mixture was heated to 100° C. for about 3 h by which time, the reaction was complete as judged by TLC. Excess water was added to the reaction mixture and the product was filtered, suck dried. The crude was passed through a short column of silica gel using $CH_2Cl_2$ as eluent (Solid; 84 g; 72%).

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A process for the synthesis of Oroxylin A as represented by STR#1, comprising steps of;
   a) esterifying Baicalin, as represented by STR#2 using acid-alcohol mixture to obtain a compound as represented by STR#3,

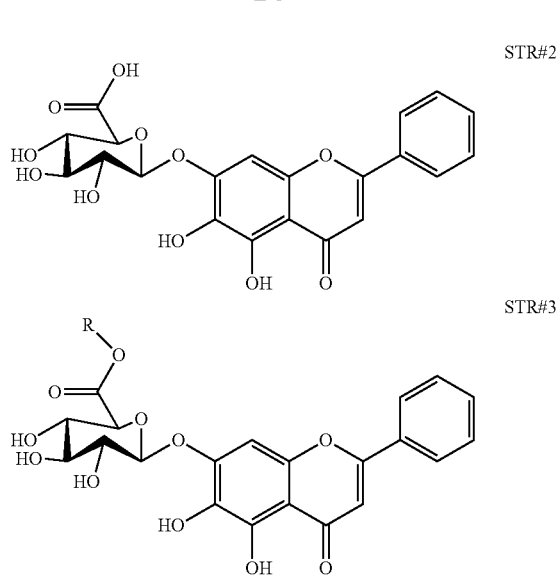

wherein 'R' is selected from methyl, ethyl, n-propyl or isopropyl;
   b) methylating the compound of step a) represented by STR#3 using a methylating agent in the presence of a base to obtain a compound as represented by STR#4,

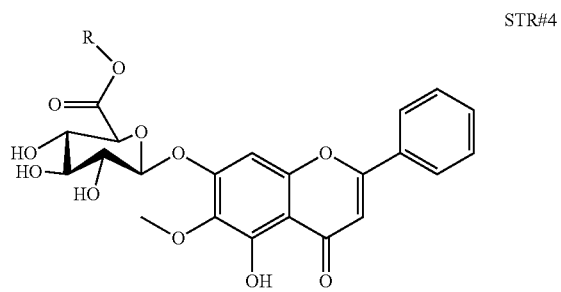

wherein 'R' is selected from methyl, ethyl, n-propyl of isopropyl;
   c. subjecting the compound of step b, represented by STR#4 to acid hydrolysis to obtain the product Oroxylin A as represented by STR#1

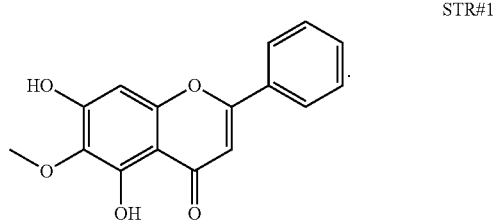 [SMILES: COc1c(O)cc2oc(-c3ccccc3)cc(=O)c2c1O]

2. The method as in claim 1, wherein the acid is selected from the group consisting of sulphuric acid, p-toluene sulfonic acid, hydrochloric acid, methanesulfonic acid and trifluroacetic acid.

3. The method as in claim 1, wherein the alcohol is selected from the group consisting of methanol, ethanol, n-propanol and isopropanol.

4. The method as in claim 1, wherein the methylating agents are selected from the group consisting of dimethyl sulphate, methyl iodide, dimethyl carbonate, diazomethane and trimethylsilyldiazomethane.

5. The method as in claim 1, wherein the base is selected from the group consisting of potassium carbonate, sodium carbonate, cesium carbonate, triethyl amine and di-isopropyl amine.

* * * * *